(12) United States Patent
Pullagurla et al.

(10) Patent No.: US 8,633,239 B2
(45) Date of Patent: Jan. 21, 2014

(54) PROCESS FOR THE PREPARATION OF ELETRIPTAN

(75) Inventors: Manik Reddy Pullagurla, Andhra Pradesh (IN); Jagadeesh Babu Rangisetty, Andhra Pradesh (IN); Neelam Naidu, Andhra Pradesh (IN); Nagaraju Maddela, Andhra Pradesh (IN); Radha Nagarapu, Andhra Pradesh (IN); Pulla Rao Polagani, Andhra Pradesh (IN)

(73) Assignee: Biophore India Pharmaceuticals Private Limited, Hyderabad (IN)

( * ) Notice: Subject to any disclaimer, the term of this patent is extended or adjusted under 35 U.S.C. 154(b) by 354 days.

(21) Appl. No.: 12/998,522

(22) PCT Filed: Oct. 29, 2009

(86) PCT No.: PCT/IN2009/000614
§ 371 (c)(1),
(2), (4) Date: Apr. 28, 2011

(87) PCT Pub. No.: WO2010/049952
PCT Pub. Date: May 6, 2010

(65) Prior Publication Data
US 2011/0207943 A1 Aug. 25, 2011

(30) Foreign Application Priority Data
Oct. 31, 2008 (IN) .......................... 2654/CHE/2008

(51) Int. Cl.
*A61K 31/4025* (2006.01)
*C07D 403/02* (2006.01)
*C07D 209/10* (2006.01)
*A61K 31/404* (2006.01)

(52) U.S. Cl.
USPC ........................ 514/414; 548/468; 548/516

(58) Field of Classification Search
None
See application file for complete search history.

(56) References Cited

U.S. PATENT DOCUMENTS 5,545,644 A 8/1996 Macor et al.
6,201,131 B1 3/2001 Otera et al.
7,288,662 B2 10/2007 Ogilvie

FOREIGN PATENT DOCUMENTS

WO 2005/103035 A1 11/2005

OTHER PUBLICATIONS

Pavia, et al., Introduction to Organic Laboratory Techniques a Microscale Approach, First Ed. pp. 617-637 at 633 (1990).*

(Continued)

*Primary Examiner* — Michael Barker
(74) *Attorney, Agent, or Firm* — Davidson, Davidson & Kappel, LLC

(57) ABSTRACT

The present invention relates to a novel process for the preparation of (R)-3-((1-methylpyrrolidin-2-yl)methyl)-5-(2-(phenylsulfonyl)ethyl)-1H-indole and its intermediates thereof.

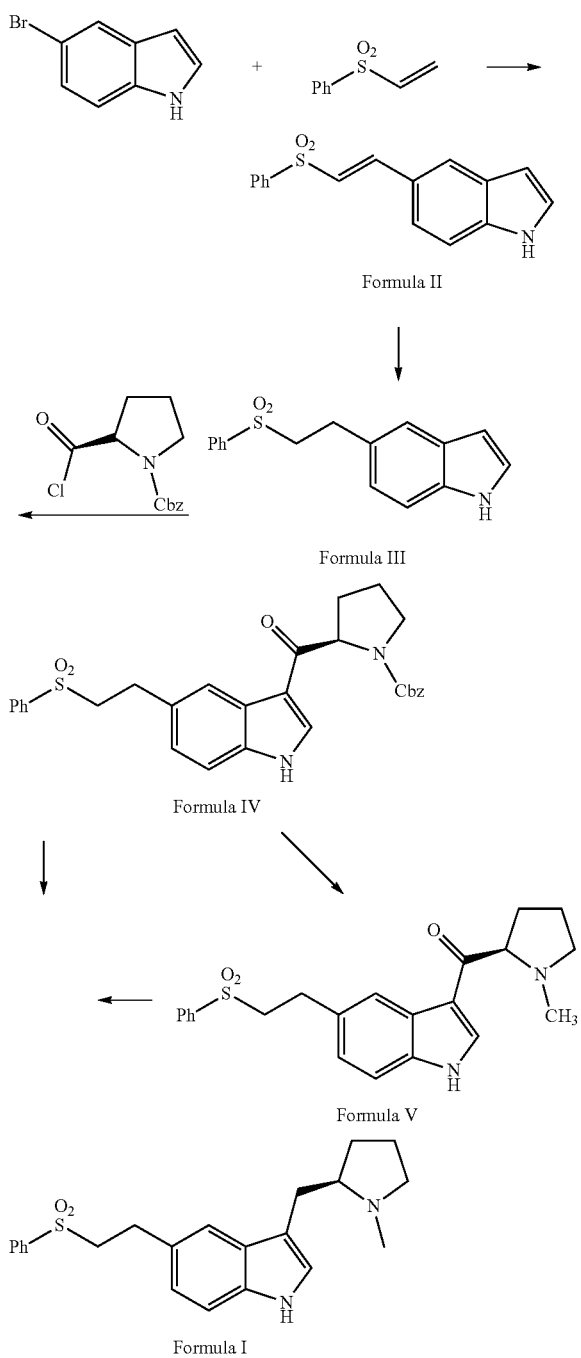

9 Claims, No Drawings

(56) References Cited

OTHER PUBLICATIONS

"Contemporary Drug Synthesis", Wiley-Interscience, XP008124053, Jun. 25, 2004, pp. 161-187.

Guy R. Humphrey et al., "Practical Methodologies for the Synthesis of Indoles", Chemical Reviews, Jul. 2006, vol. 106, No. 7, pp. 2875-2911.

International Search Report for PCT/IN2009/000614, mailed Jul. 10, 2010.

* cited by examiner

PROCESS FOR THE PREPARATION OF ELETRIPTAN

CROSS REFERENCE TO RELATED APPLICATIONS

This application is a national stage application, filed under 35 U.S.C. §371 of International Application PCT/IN2009/000614, filed Oct. 29, 2009, which claimed priority to Indian Application No. 2654/CHE/2008, filed Oct. 31, 2008, the disclosures of which are hereby incorporated by reference.

FIELD OF INVENTION

The present invention relates to a novel process for the preparation of (R)-3-((1-methylpyrrolidin-2-yl)methyl)-5-(2-(phenylsulfonyl)ethyl)-1H-indole and its intermediates thereof.

BACKGROUND

Eletriptan is an anti-migraine drug marketed as Relpax and is currently marketed in over 50 countries worldwide. It belongs to the triptan class of drugs that also includes sumatriptan, naratriptan, rizatriptan, almotriptan, zolmitriptan and frovatriptan. The present invention relates to a novel process for the synthesis of Eletriptan (Formula I) which provides significant advantages over the existing processes.

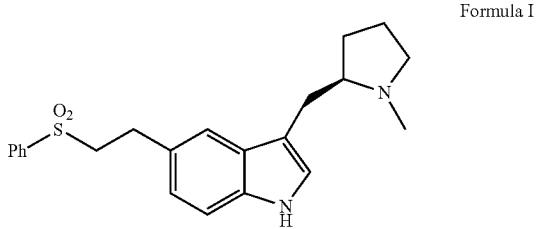 [SMILES: CN1CCC[C@@H]1Cc1c[nH]c2ccc(CCS(=O)(=O)c3ccccc3)cc12]

Formula I

STATE OF THE ART

The following patents and applications describe synthesis of Eletriptan.

U.S. Pat. No. 5,545,644A1 describes a synthetic process for Eletriptan. 5-Bromoindole was acylated at the 3-position by reacting the magnesium salt of 5-bromoindole. This process results in a dimer formation in the final Pd/C reduction stage which poses problems in purification which further leads to decrease in yields.

U.S. Pat. No. 7,288,662B2 discloses methods to circumvent the problems associated with dimer formation described in U.S. Pat. No. 5,545,644A1. The indole-nitrogen was acetylated prior to hydrogenation and later deacetylated to give pure Eletriptan. However, this process introduced two additional steps into the synthesis which is time consuming and subsequently costly.

WO2005/103035A1 discloses Eletriptan synthesis by a Fischer Indole process. However, enantiomeric purity of the finished product depends on the purity of an acetal intermediate which might require asymmetric synthesis or optical resolution. Eletriptan obtained in the reported procedure had about 94% enantiomeric excess.

Therefore there is a need for an efficient and convenient synthesis of Eletriptan.

SUMMARY OF THE INVENTION

In light of the foregoing deficiencies in the art, one of the objects of the invention was to provide a process for preparing optically pure Eletriptan.

Another object of the invention was to develop a process devoid of any dimer impurity and provide an improved method for the synthesis of Eletriptan.

Yet another object of the invention was to develop shortest possible synthetic route to obtain Eletriptan which is commercially viable.

In one embodiment this invention provides an alternative method for preparing Eletriptan which may be represented as shown in Scheme I. 5-Bromoindole under Heck reaction conditions is coupled with phenyl vinyl sulfone followed by acylation with Cbz-Proline acid chloride to obtain a compound of Formula IV which on reduction in presence of a hydride agent provide Eletriptan.

Scheme I

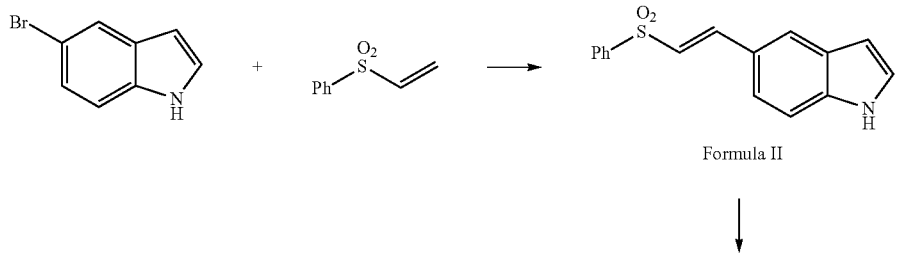

Formula II

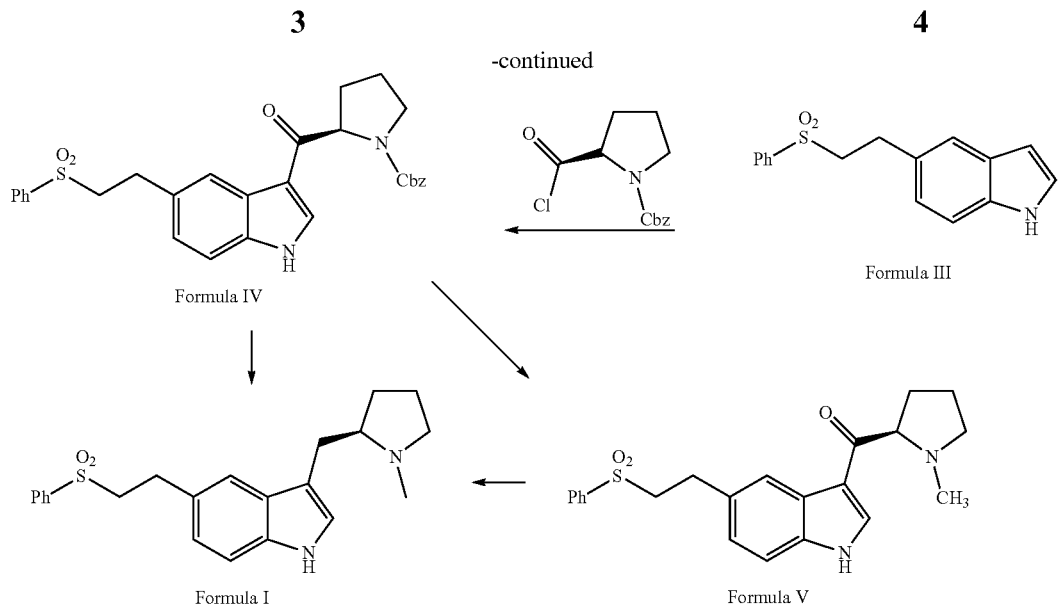

Formula IV

Formula III

Formula I

Formula V

To reduce the dimer formation (VI), 5-bromoindole is coupled with phenyl vinyl sulfone to give the compound of Formula II. The compound of Formula II was hydrogenated to give the compound of Formula III. The product was conveniently isolated as a solid. Surprisingly this method did not result in significant dimer (VI) formation and this process was found particularly advantageous. The yields in both the steps were in the range of 60-90%.

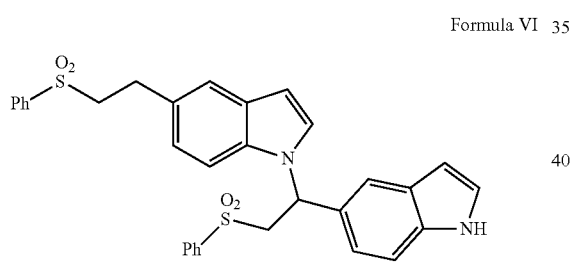

Formula VI

The proline side chain was then attached to the compound of Formula III in the presence of a Grignard's reagent and a Lewis acid to give the compound of Formula IV. This on reduction in the presence of a reducing agent gave Eletriptan.

Alternately, compound of Formula IV is catalytically reduced to compound of Formula V which is subsequently converted to Eletriptan.

The current process surprisingly did not result in the dimer impurity observed in the earlier processes and also did not need the acetylation of indole N1-position. The current process offers significant advantages in terms of purity and cost efficiency and circumvents the problems associated with prior art processes.

Preparation of Compound of Formula II

According to one aspect of the invention preparation of compound of Formula II can be carried out under Heck reaction conditions in presence of a suitable palladium or a nickel coupling catalyst, phenyl vinyl sulfone and a base. The reaction can be carried out in acetonitrile, toluene, DMF, DME, DMAc preferably in DMF or acetonitirle at temperatures of 50-120 C. The reaction can be achieved in presence of a suitable base selected from the group comprising $K_2CO_3$, $Na_2CO_3$, KOAc, NaOAc, $Cs_2CO_3$, DABCO, DIPEA, and TEA. The base is preferably DIPEA and the coupling catalyst is preferably a palladium metal catalyst. Surprisingly a reasonably pure compound was obtained without the indole 3-position and indole N1-position substitution.

Preparation of Compound of Formula III

According to another aspect of the invention compound of Formula III may be obtained by catalytic reduction of compound of Formula II by hydrogen or hydrogen source in presence of a suitable catalyst such as Pd/C, Raney nickel, palladium hydroxide, platinum catalyst, rhodium, and ruthenium. The reduction can also be achieved in presence of diborane, $NaBH_4$, $LiBH_4$, $NaCNBH_3$, sodium triacetoxyborohydride or a suitable hydride reducing reagent. The reaction can be carried out at temperatures of 20-100° C. and 15-100 psi hydrogen pressure. The reaction is preferably carried out in presence of 10% Pd/C at 20-30° C. at 40-80 psi. The reaction can be carried out in alcohols, THF, ethyl acetate, acetone, acetonitrile or combinations thereof and preferably in methanol According to another aspect of the invention, the novel compound of Formula III is characterized by the $^1$H NMR $CDCl_3$ δ=8.15 (bs, NH), 7.93-8.00 (m, 2H), 7.53-7.70 (m, 3H), 7.38 (s, 1H), 7.30 (d, 1H), 7.20 (dd, 1H), 6.93 (dd, 1H), 6.42-6.48 (m, 1H), 3.37-3.46 (m, 2H), 2.99-3.17 (m, 2H). ESI Mass (M+23) 308.4

A further aspect of the invention is the reaction does not require any acid in the reaction where such use could poison the catalyst, which was an aspect of previous inventions to obtain Eletriptan.

Preparation of Compound of Formula IV

The compound of Formula IV is prepared by reaction of the magnesium salt of indole derivative with n-protected proline acid chloride. Magnesium salt of Formula III is prepared in presence of alkyl magnesium halides like methyl, ethyl, propyl magnesium halides or aryl magnesium halides like phenyl or substituted phenyl magnesium halides preferably ethyl magnesium bromide. The reaction is preferably carried out in presence of a Lewis acid such as $AlCl_3$, $ZnCl_2$, $SnCl_4$, $BBr_3$ and preferably in presence of $ZnCl_2$. The reaction is carried out in presence of a solvent selected from the group comprising THF, diethyl ether, dichloromethane, toluene or combinations thereof, preferably in dichloromethane and THF or dichloromethane and diethyl ether.

According to another aspect of the invention, the novel compound of Formula IV is characterized by the $^1$H NMR CDCl$_3$ δ=9.85 (bs, NH), 7.92-7.99 (m, 2H), 7.54-7.80 (m, 5H), 7.28-7.43 (m, 4H), 6.78-7.08 (m, 3H), 4.89-5.28 (m, 3H), 3.53-3.80 (m, 2H), 3.25-3.48 (m, 2H), 2.91-3.19 (m, 2H), 1.70-2.35 (m, 4H). ESI Mass (M–H) 515.6, (M+23) 539.2

According to another aspect of the invention Formula V used in the process may be obtained by catalytic reduction of Formula IV under hydrogen or hydrogen source in presence of a suitable catalyst such as Pd/C, Raney nickel, palladium hydroxide, platinum catalyst, rhodium, and ruthenium, and a suitable solvent. The reduction can also be achieved in presence of diborane, NaBH$_4$, LiBH$_4$, NaCNBH$_3$, sodium triacetoxyborohydride or a suitable hydride reducing reagent. The reaction can be carried out at temperatures of 20-100° C. and 15-80 psi hydrogen pressure. The reaction can be carried out, but not limited to, in alcohols, ethers or mixtures thereof. The most suitable solvents are methanol, ethanol, THF or mixtures thereof. The reaction is preferably carried out in presence of 10% Pd/C in methanol at 20-30° C. at 40-60 psi.

Compound of Formula I is obtained by reduction of Formula IV. The reaction is carried out in the presence of a suitable reducing agent and preferably in a suitable solvent. The solvent chosen for the reaction includes THF, diethyl ether, diisopropyl ether, dichloromethane, 1,4-dioxane, methyl THF and 1,2-dimethoxyethane preferably in THF at 0-65 C. The reducing agent is preferably a hydride reducing agent and selected from the group comprising LiAlH$_4$, NaBH$_4$, LiBH$_4$, NaCNBH$_3$, sodium triacetoxyborohydride and the like and most preferably LiAlH$_4$.

Alternatively, compound of Formula I is obtained by reduction of Formula V. The reaction is carried out in the presence of a suitable reducing agent and preferably in a suitable solvent. The solvent chosen for the reaction includes THF, diethyl ether, diisopropyl ether, dichloromethane, 1,4-dioxane, methyl THF and 1,2-dimethoxyethane preferably in THF at 0-65 C. The reducing agent is preferably a hydride reducing agent and selected from the group comprising LiAlH$_4$, NaBH$_4$, LiBH$_4$, NaCNBH$_3$, sodium triacetoxyborohydride and the like and most preferably LiAlH$_4$.

Purification of Eletriptan

Another aspect of the invention is the purification of the Eletriptan free base via salt-base conversion. Eletriptan free base obtained by the process of the invention is converted into a suitable salt formed by an organic acid such as oxalate, fumarate, maleate or the like, preferably an oxalate salt followed by conversion to free base by treatment with a suitable base. Eletriptan oxalate is the most preferred salt and the most suitable base is selected from the group comprising NaOH, KOH, Na$_2$CO$_3$, K$_2$CO$_3$, ammonia solution/NH$_4$OH. Eletriptan free base thus obtained has HPLC purity greater than 95%.

The process of the invention is illustrated by the following examples to obtain Eletriptan.

EXAMPLE 1

(E)-5-(2-(phenylsulfonyl)vinyl)-1H-indole (Formula II)

A solution of 5-bromoindole (5.0 g, 25.5 mmol), phenylvinylsulfone (7.50 g, 44.64 mmol), Pd(OAc)$_2$ (0.46 g, 2.05 mmol), tri-O-tolylphosphine (1.55 g, 5.10 mmol) and triethylamine (4.88 g, 48.46 mmol) was heated to 95-105° C. for 6-15 h in DMF. The reaction mixture was cooled to RT, diluted with dichloromethane and filtered over a bed of filter aid. The filtrate was sequentially washed with water and brine, and dried over sodium sulphate. The organic layer was concentrated under vacuum and the product precipitated from dichloromethane and hexane as a solid in about 85-90% yield.

EXAMPLE 2

(E)-5-(2-(phenylsulfonyl)vinyl)-1H-indole (Formula II)

A solution of 5-bromoindole (5.0 g, 25.5 mmol), phenylvinylsulfone (7.50 g, 44.64 mmol), Pd(OAc)$_2$ (0.46 g, 2.05 mmol), tri-O-tolylphosphine (1.55 g, 5.10 mmol) and DIPEA (3.6 g) was heated to reflux for 18 h in acetonitrile. The reaction mixture was cooled to RT, diluted with dichloromethane and filtered over a bed of filter aid. The solvent is completely distilled off and to the crude fresh dichloromethane was charged. The filtrate was sequentially washed with water and brine, and dried over sodium sulphate. The organic layer was concentrated under vacuum and the product precipitated from ethylacetate and hexane as a solid in about 65-70% yield.

EXAMPLE 3

5-(2-(phenylsulfonyl)ethyl)-1H-indole (Formula III)

A suspension of (E)-5-(2-(phenylsulfonyl)vinyl)-1H-indole (5.0 g) in 50 ml methanol, 10 ml THF and 10% Pd/C (1.0 g) was subject to hydrogenation at 45-50 psi. Upon completion of the reaction the catalyst was filtered off and the solvent removed under vacuum to provide the title compound in about 85-90% yield as an off-white solid. $^1$H NMR CDCl$_3$ δ=8.15 (bs, NH), 7.93-8.00 (m, 2H), 7.53-7.70 (m, 3H), 7.38 (s, 1H), 7.30 (d, 1H), 7.20 (dd, 1H), 6.93 (dd, 1H), 6.42-6.48 (m, 1H), 3.37-3.46 (m, 2H), 2.99-3.17 (m, 2H). ESI Mass (M+23) 308.4

EXAMPLE 4

(R)-benzyl2-(5-(2-(phenylsulfonyl)ethyl)-1H-indole-3-carbonyl)pyrrolidine-1-carboxylate (Formula Iv)

To a solution of CBZ-D-Proline (1.56 g, 8.0 mmol) in dichloromethane was charged oxalyl chloride (4 ml, 44.2 mmol) and allowed to stir are RT for 1 h. The solvent was distilled off and the reaction mass diluted with 10 ml dichloromethane.

In a separate setup ethyl magnesium bromide (7.0 ml of a 3M solution in ether) was charged slowly to a solution of 5-(2-(phenylsulfonyl)ethyl)-1H-indole (1.0 g, 3.4 mmol) in dichloromethane. The reaction mixture was heated at reflux for 30 min. The reaction was cooled to –20° C. and ZnCl$_2$ followed by the above prepared CBZ-prolinyl acid chloride in dichloromethane was charged slowly to the reaction at –20° C. The resulting solution was stirred at –15 to –25° C. for 10 h. The completion of the reaction was monitored by TLC. The reaction mass was warmed to RT and diluted with 20 ml dichloromethane. The organic layer was sequentially washed sat. ammonium chloride solution, sat. sodium bicarbonate solution and brine. The organic layer was dried over sodium sulphate and concentrated under vacuum to give a pure product in about 40-75% yield. $^1$H NMR CDCl$_3$ δ=9.85 (bs, NH), 7.92-7.99 (m, 2H), 7.54-7.80 (m, 5H), 7.28-7.43 (m, 4H), 6.78-7.08 (m, 3H), 4.89-5.28 (m, 3H), 3.53-3.80 (m, 2H), 3.25-3.48 (m, 2H), 2.91-3.19 (m, 2H), 1.70-2.35 (m, 4H). ESI Mass (M−H) 515.6, (M+23) 539.2

EXAMPLE 5

(R)-3-((1-methylpyrrolidin-2-yl)methyl)-5-(2-(phenylsulfonyl)ethyl)-1H-indole (Formula I)

To a suspension of LAH (1.46 g, 38.8 mmol) and THF (10 ml) was slowly charged (R)-benzyl 2-(5-(2-(phenylsulfonyl)ethyl)-1H-indole-3-carbonyl)pyrrolidine-1-carboxylate (2.0 g, 3.8 mmol) at 0° C. and then the reaction was slowly heated to reflux. Upon completion of the reaction in about 3-5 h, the reaction was cooled to 0-5° C. and 1N NaOH solution and H$_2$O were sequentially charged. The solids were filtered and the precipitate washed with additional THF. The filtrate was distilled to dryness under reduced pressure. The residue was dissolved in water and the aqueous layer extracted with dichloromethane and dried over sodium sulfate and distilled to) give a crude compound. The residue obtained is dissolved in dichloromethane and 1.0 eq oxalic acid is added to provide an oxalate salt. The oxalate crude is washed with diethyl ether. The oxalate salt is then dissolved in water and the solution made basic and the product extracted into dichloromethane. The organic layer is dried over sodium sulfate and distilled to provide the title compound in 75-80% yield with >95% purity. $^1$H NMR CDCl$_3$ δ=8.10 (bs, NH), 7.92-7.99 (m, 2H), 7.62-7.69 (m, 1H), 7.53-7.61 (m, 2H), 7.30 (s, 1H), 7.22 (d, 1H), 7.03 (s, 1H), 6.93 (dd, 1H), 3.38-3.45 (m, 2H), 3.09-3.21 (m, 4H), 2.45-2.55 (m, 2H), 2.45 (s, 3H), 2.20-2.30 (m, 1H), 1.50-1.90 (m, 4H). ESI Mass (M+H) 383.69

EXAMPLE 6

(R)-(1-methylpyrrolidin-2-yl)(5-(2-(phenylsulfonyl)ethyl)-1H-indol-3-yl)methanone (Formula V)

A suspension of (R)-benzyl-2-(5-(2-(phenylsulfonyl)ethyl)-1H-indole-3-carbonyl)-pyrrolidine-1-carboxylate (5.0 g) in 50 ml acetone, methanesulfonic acid, formaldehyde and 10% Pd/C was subject to hydrogenation at 45 psi. Upon completion of the reaction the catalyst was filtered off and the solvent removed under vacuum to provide the title compound in about 65-75% yield. Mass (M+Na) 419.5

EXAMPLE 7

(R)-3-((1-methylpyrrolidin-2-yl)methyl)-5-(2-(phenylsulfonyl)ethyl)-1H-indole (Formula I)

To a suspension of LAH and THF was slowly charged (R)-(1-methylpyrrolidin-2-yl)(5-(2-(phenylsulfonyl)ethyl)-1H-indol-3-yl)methanone at 0° C. and then the reaction was slowly heated to reflux. Upon completion of the reaction in about 3-5 h, the reaction was cooled to 0-5° C. and 1N NaOH soln and H$_2$O were sequentially charged. The solids were filtered and the precipitate washed with additional THF. The filtrate was distilled to dryness under reduced pressure. The residue was dissolved in water and the aqueous layer extracted with dichloromethane and dried over sodium sulfate and distilled to give the title compound in 75-80% yield.

We claim:
1. A compound of formula III

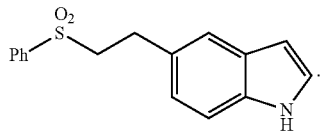

Formula III

2. A compound of formula IV

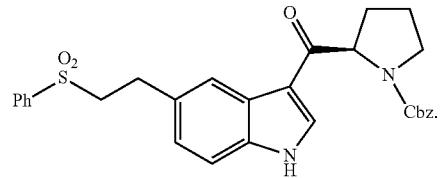

Formula IV

3. A process for preparation of Eletriptan free base (Formula I) comprising:

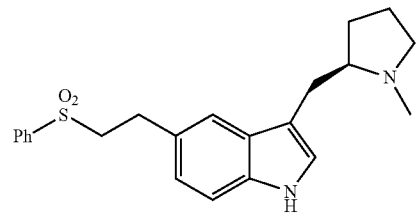

Formula I (a) reacting 5-bromoindole with phenyl vinyl sulfone under Heck reaction conditions in the presence of a coupling catalyst and a base to obtain a compound of Formula II;

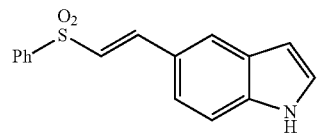

Formula II (b) reduction of compound of Formula II in the presence of a catalytic reducing agent or a hydride reducing agent to a compound of Formula III;

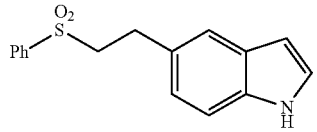

Formula III (c) formation of compound of Formula IV from the compound of Formula III in presence of a Grignard reagent and a Lewis acid via the magnesium salt of Formula III as an intermediate;

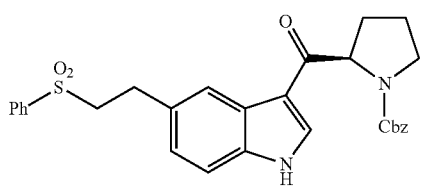

Formula IV (d) reduction of compound of Formula IV in the presence of a reducing agent and solvent to obtain Eletriptan compound of Formula I.

4. The process of claim 3, wherein the coupling catalyst used in step (a) is palladium or a nickel catalyst and the base employed is selected from the group consisting of $K_2CO_3$, $Na_2CO_3$, KOAc, NaOAc, $Cs_2CO_3$, 1,4-Diazabicyclo[2.2.2]octane (DABCO), N,N-Diisopropylethylamine (DIPEA), and Triethylamine (TEA).

5. The process of claim 3, wherein the reducing agent in the step (b) is either a catalytic reducing agent or a hydride reducing agent.

6. The process of claim 3, wherein the magnesium salt of Formula III is prepared in presence of alkyl magnesium halides or aryl magnesium halides selected from the group consisting of methyl, ethyl, propyl magnesium halides, phenyl magnesium halides and substituted phenyl magnesium halides.

7. The process of claim 3, wherein the Lewis acid employed in step (c) is selected from the group consisting of $AlCl_3$, $ZnCl_2$, $SnCl_4$ and $BBr_3$.

8. The process of claim 3, wherein the reducing agent in step (d) is selected from the group consisting of $LiAlH_4$, $NaBH_4$, $LiBH_4$, $NaCNBH_3$ and sodium triacetoxyborohydride.

9. The process of claim 3, wherein the solvent in step (d) is selected from the group consisting of THF, diethyl ether, dichloromethane and toluene or combinations thereof.

\* \* \* \* \*